Figure 1:
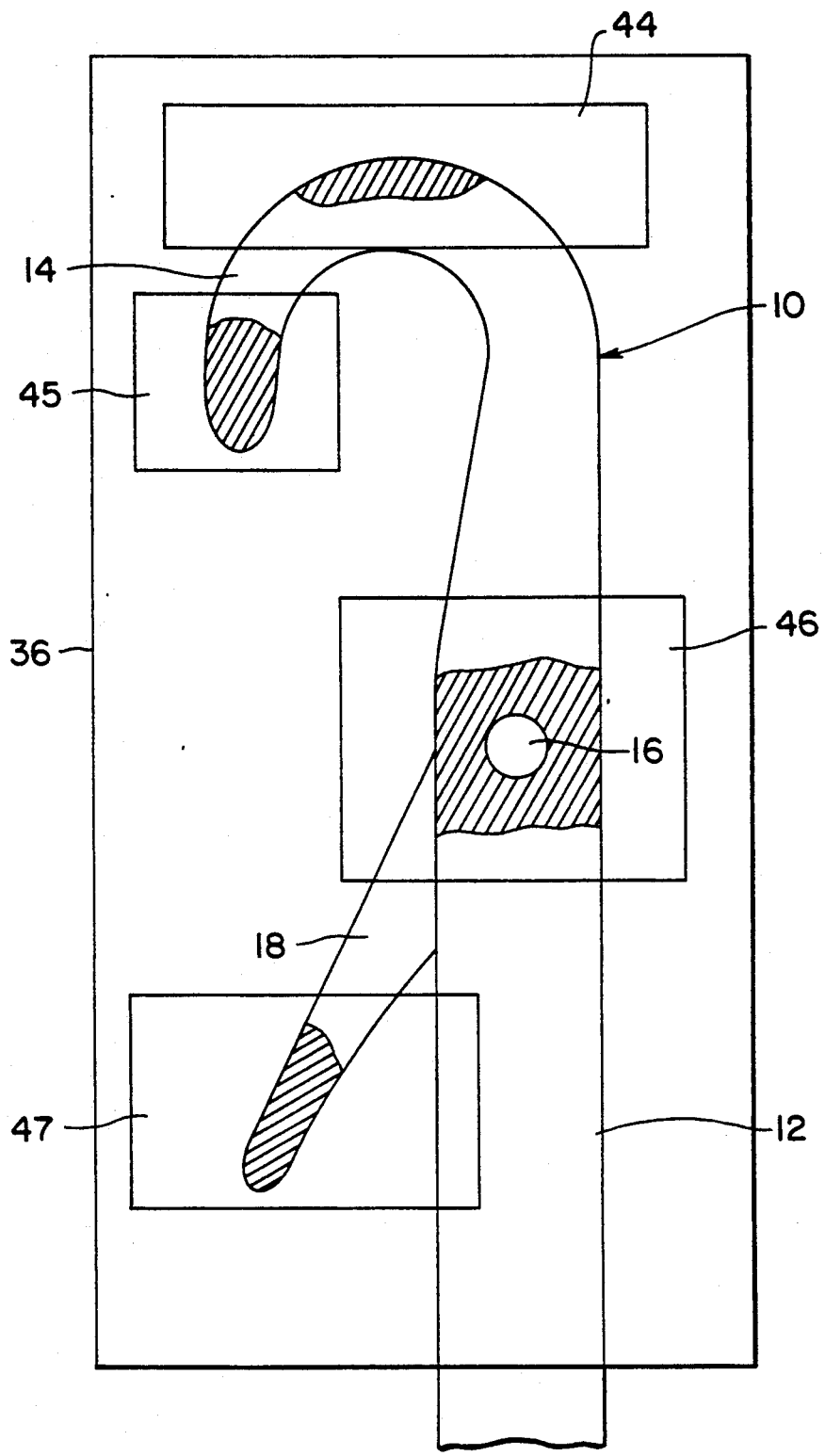

United States Patent [19]
Massen

[11] Patent Number: 5,333,208
[45] Date of Patent: Jul. 26, 1994

[54] METHOD AND ARRANGEMENT FOR OPTICAL CONTROL OF THE NEEDLES OF KNITTING MACHINES

[75] Inventor: Robert Massen, Radolfzell, Fed. Rep. of Germany

[73] Assignees: Theodor Grosz & Sohne; Ernst Beckert Nadelfabrik Commandit-Gesellschaft, Albstadt-Ebingen, Fed. Rep. of Germany

[21] Appl. No.: 117,645

[22] Filed: Sep. 8, 1993

Related U.S. Application Data

[63] Continuation of Ser. No. 696,021, May 6, 1991, abandoned.

[30] Foreign Application Priority Data

May 8, 1990 [DE] Fed. Rep. of Germany ....... 4014661

[51] Int. Cl.$^5$ .............................................. G06K 9/00
[52] U.S. Cl. ........................................... 382/8; 382/1; 348/88; 348/92; 348/125
[58] Field of Search ............................ 382/8, 1, 34, 57; 358/101, 106; 356/23; 250/224; G06K 9/00, 9/68; H04N 7/00, 7/18; G01P 3/40

[56] References Cited

U.S. PATENT DOCUMENTS

| 3,427,462 | 2/1969 | Cist | 250/562 |
|---|---|---|---|
| 3,946,578 | 3/1976 | Venczel | 66/157 |
| 4,486,776 | 12/1984 | Yoshida | 358/106 |
| 4,649,621 | 3/1987 | Dusel et al. | 382/8 |
| 4,668,982 | 5/1987 | Tinnerino | 358/106 |
| 4,893,346 | 1/1990 | Bishop | 382/8 |
| 5,007,096 | 4/1991 | Yoshida | 382/1 |

FOREIGN PATENT DOCUMENTS

| 0265302 | 4/1988 | European Pat. Off. . |
| 3814898 | 11/1989 | Fed. Rep. of Germany . |
| 62-191743 | 8/1987 | Japan . |
| 1190806 | 5/1970 | United Kingdom . |

*Primary Examiner*—Yon J. Couso
*Attorney, Agent, or Firm*—Sixbey, Friedman, Leedom & Ferguson

[57] ABSTRACT

For controlling the quality of the needles of a knitting machine a test image of each needle is acquired with the aid of an image sensor when the needle is moved out of its rest position for forming a stitch. The analog image signals obtained on reading out the image sensor are converted to digital pixel signals, and the digital pixel signals of the test image or of individual test zones of the test image are processed for recovering information on the state of the particular needle being imaged. By using a coarse resolution image sensor it is possible to detect major faults during the normal operation of the knitting machine at full working speed. Needles exhibiting wear and minor faults can be detected by using a high resolution image sensor during special inspection times in which the knitting machine is operated at reduced speed.

18 Claims, 6 Drawing Sheets

METHOD AND ARRANGEMENT FOR OPTICAL CONTROL OF THE NEEDLES OF KNITTING MACHINES

This application is a continuation of Ser. No. 07/696,021, filed May 6, 1991, now abandoned.

The invention relates to a method for optical quality control of the needles of knitting machines and an arrangement for carrying out the method.

Knitting machines are highspeed precision machines for producing knitted fabrics which use a very large number mechanically lastly moving precision needles which in a flat knitting machine are arranged along a linear path and in a circular knitting machine are arranged in a circle. To form a stitch course the needles are consecutively individually moved out of their rest position in the needle bed into a stitch forming position and back into the rest position. With several thousand needles per needle bed the needle movement frequency is of the order of magnitude of 10 kHz. To avoid the production of faulty fabric the dynamically highly stressed needles must be monitored for major faults such as breakages, coarse cracks and bends, so that the knitting machine is shut down immediately on occurrence of a major fault of this type. Such major faults occur suddenly and must be detected immediately during the normal operation of the knitting machine.

In addition, it is desirable for preventive maintenance to detect needles exhibiting wear and minor faults such as fine cracks so that such needles can be replaced in good time. Wear and fine cracks occur gradually and develop slowly; in the initial stage they do not impair the quality of the knitted fabric. It is therefore not necessary during normal operation of the knitting machine at full working speed to monitor continuously any occurrence of wear and minor faults; it suffices to check for these at relatively large intervals of time, and this can also be done at reduced speed. The periodic measuring of the wear of the various needles and needle zones also provides valuable indications of the quality of the needles used, the setting of the tension, the quality of the yarns used, etc.

To detect major faults optical sensors are known which at full working speed of the knitting machine with the aid of a photodiode measure the total amount of light reflected by each needle moving into the stitch forming position; major defects or faults can then be detected from the deviation compared with predetermined tolerance values. The detection reliability of such sensors is low and a fault classification is possible only to a very restricted extent. Wear measurements requiring local measuring in the $\mu$m range are not possible at all with such optical sensors. For such wear measurements and for detecting minor faults, such as fine cracks, hitherto the needles had to be removed from the knitting machine and investigated individually. This investigation was complicated and involved long shutdown times of the knitting machine.

It is an object of the invention to provide a method and an arrangement which permit immediate detection of major faults of the needles at full working speed of the knitting machine with great reliability and furthermore are suitable for wear measurements and detection of minor faults.

According to the invention this object is achieved in that with the aid of an image sensor camera a test image of the needle portion to be monitored of the respective needle moved out of its rest position is acquired, that the analog image signals obtained on reading out the image sensor are converted to digital pixel signals and that the digital pixel signals of the test image or individual test zones of the test image are processed for recovering information on the state of the particular needle imaged.

The method according to the invention is based on the use of image-generating sensors such as semiconductor line cameras or semiconductor matrix cameras. Depending on whether major faults are to be detected at full working speed or wear measurements with high resolution are to be made, different demands are made of the image sensors used but they can all be met with various types of commercially available image sensors. For detecting major faults a low resolution of the image sensor suffices although a high image readout and processing speed of more than 10000 images per second is necessary; for wear measurements and detecting minor faults a high resolution of the image sensor is necessary although a low image readout and processing speed of for example 50 to 500 images per second is adequate.

Accordingly, the method according to the invention for continuous detection of major faults, such as breakages, coarse cracks and bends of the needles, is preferably carried out in such a manner that the test images are acquired during the operation of the knitting machine with coarse image resolution with the needle frequency or a divisor of the needle frequency, that the digital pixel signals of the test image or the test zones of the test image are compared in the rhythm of the pixel frequency with the pixel signals of at least one stored reference image, that on the basis of each comparison a quantitative similarity degree is formed and that an alarm signal is generated when the similarity degree does not reach a predetermined tolerance threshold.

On the other hand, the method according to the invention or occasional determination of the wear data and of gradually developing minor faults, such as fine cracks, is preferably carried out in such a manner that the test images are acquired with high image resolution, that the digital pixel signals of the test images or the test zones are stored, and that the stored pixel signals are evaluated to determine geometrical dimensions of the needles and/or to determine surface characteristics of the visible needle surfaces.

An arrangement for optical quality control of the needles of knitting machines according to the invention comprises an image sensor camera having an optical system and at least one image sensor and arranged on the knitting machine in such a manner that the optical system images the portion of the particular needle moving into the stitch forming position to be monitored onto the or each image sensor, a trigger device which triggers the acquisition of a test image of the needle portion to be monitored and the reading out of the image sensor when the needle reaches a predetermined position identical for all needles, an analog to digital converter connected to the output of the or each image sensor for converting the analog image signals furnished by the image sensor to digital pixel signals and by a signal processing circuit which is connected to the output of the analog to digital converter and which processes the digital pixel signals for obtaining information on the state of the particular needle acquired.

Advantageous further developments and embodiments of the method and arrangement according to the invention are characterized in the subsidiary claims.

Figure 2:
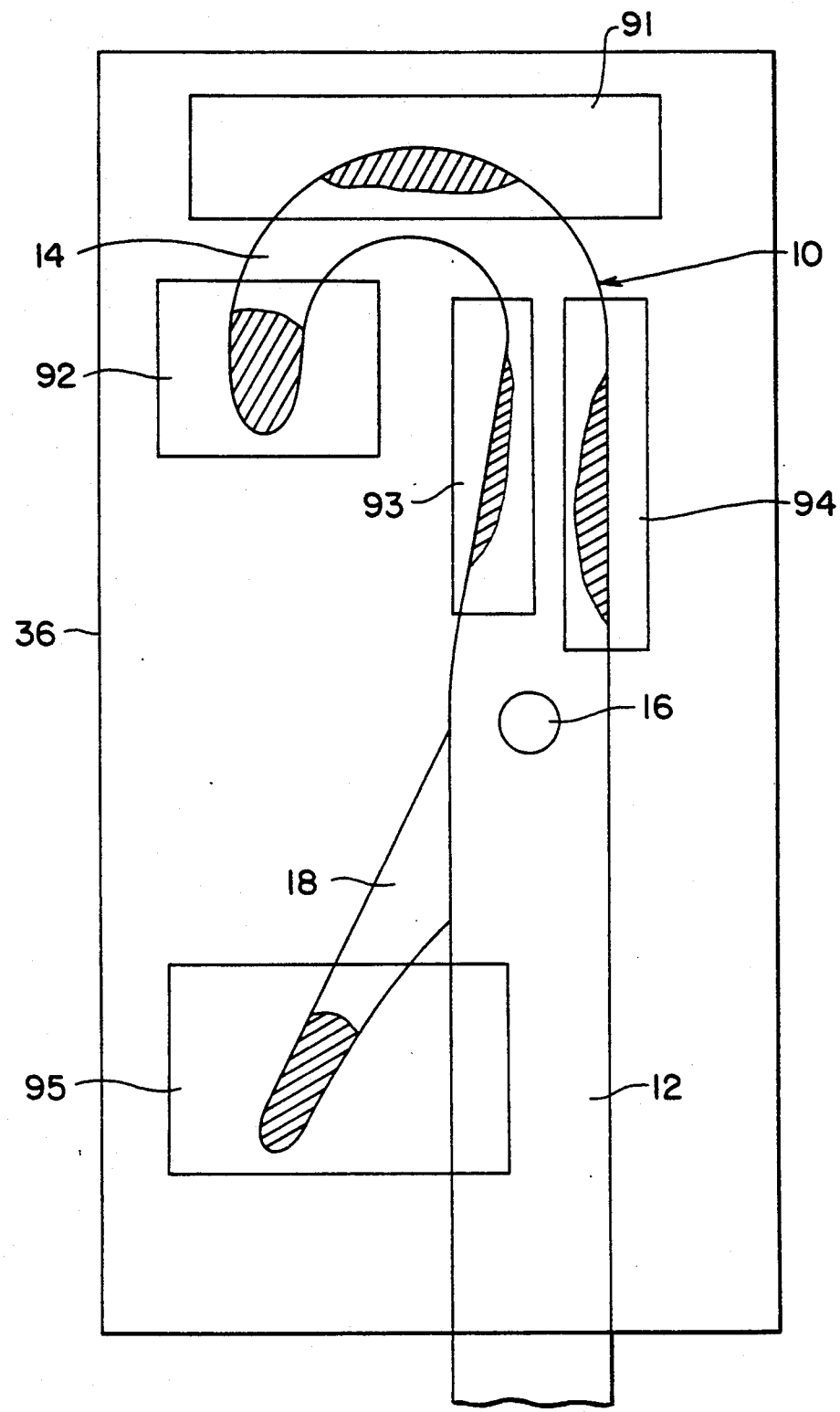
Figure 3:
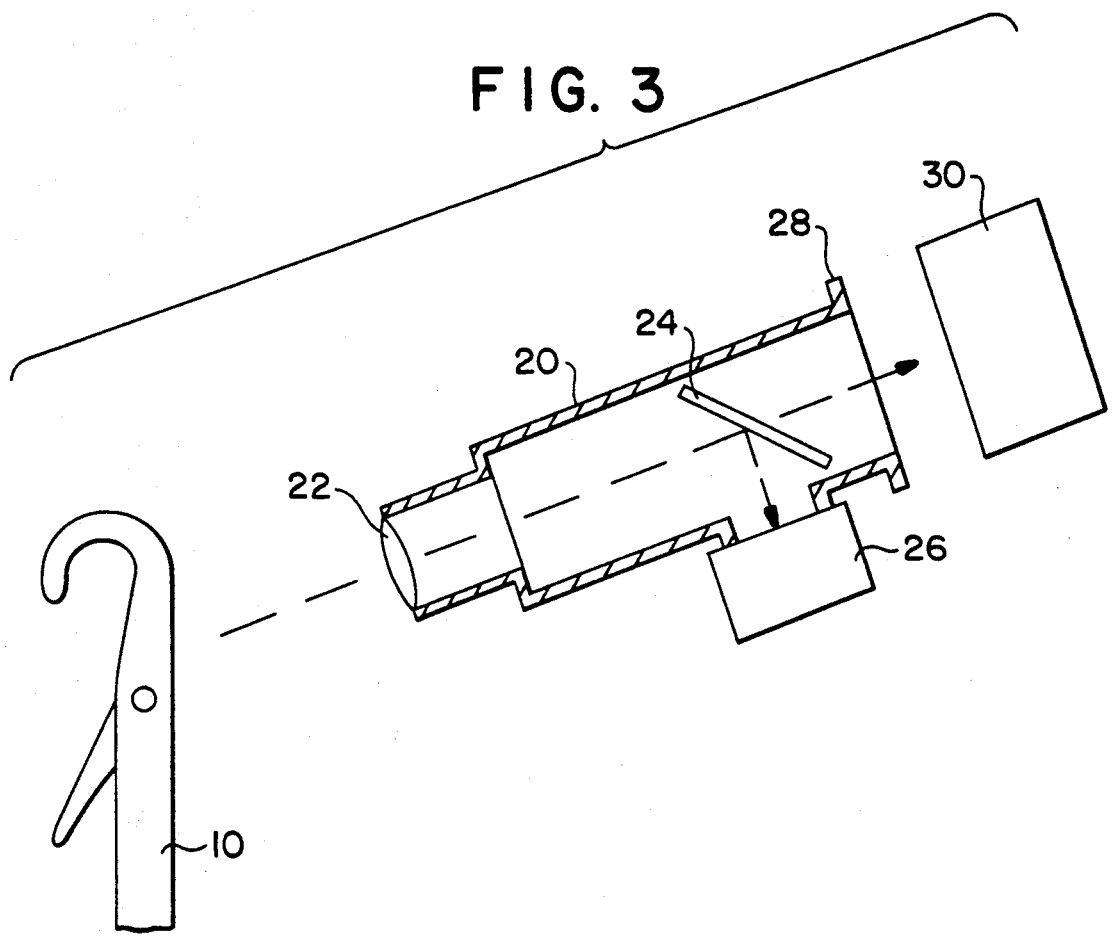
Figure 4:
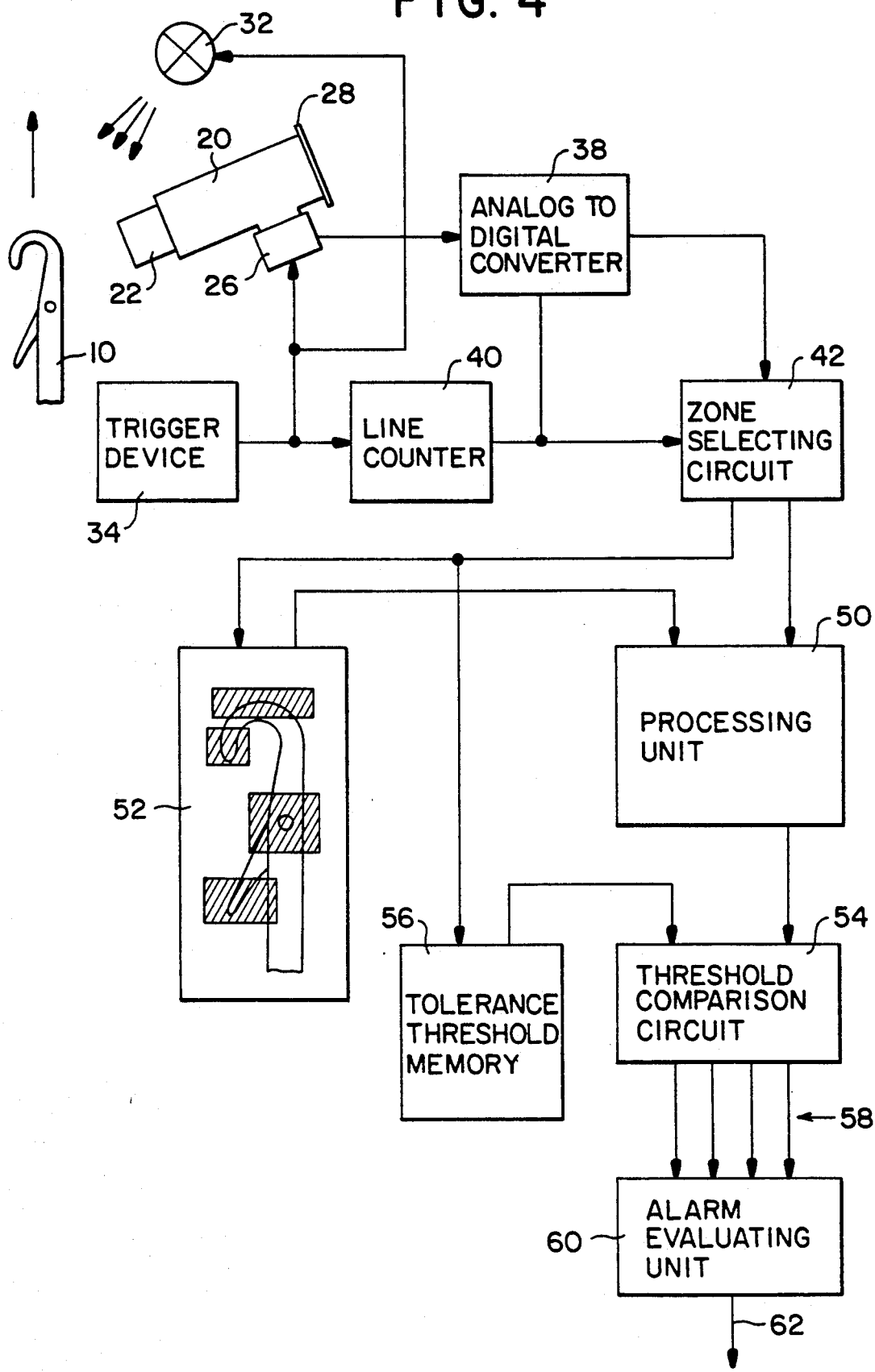
Figure 5:
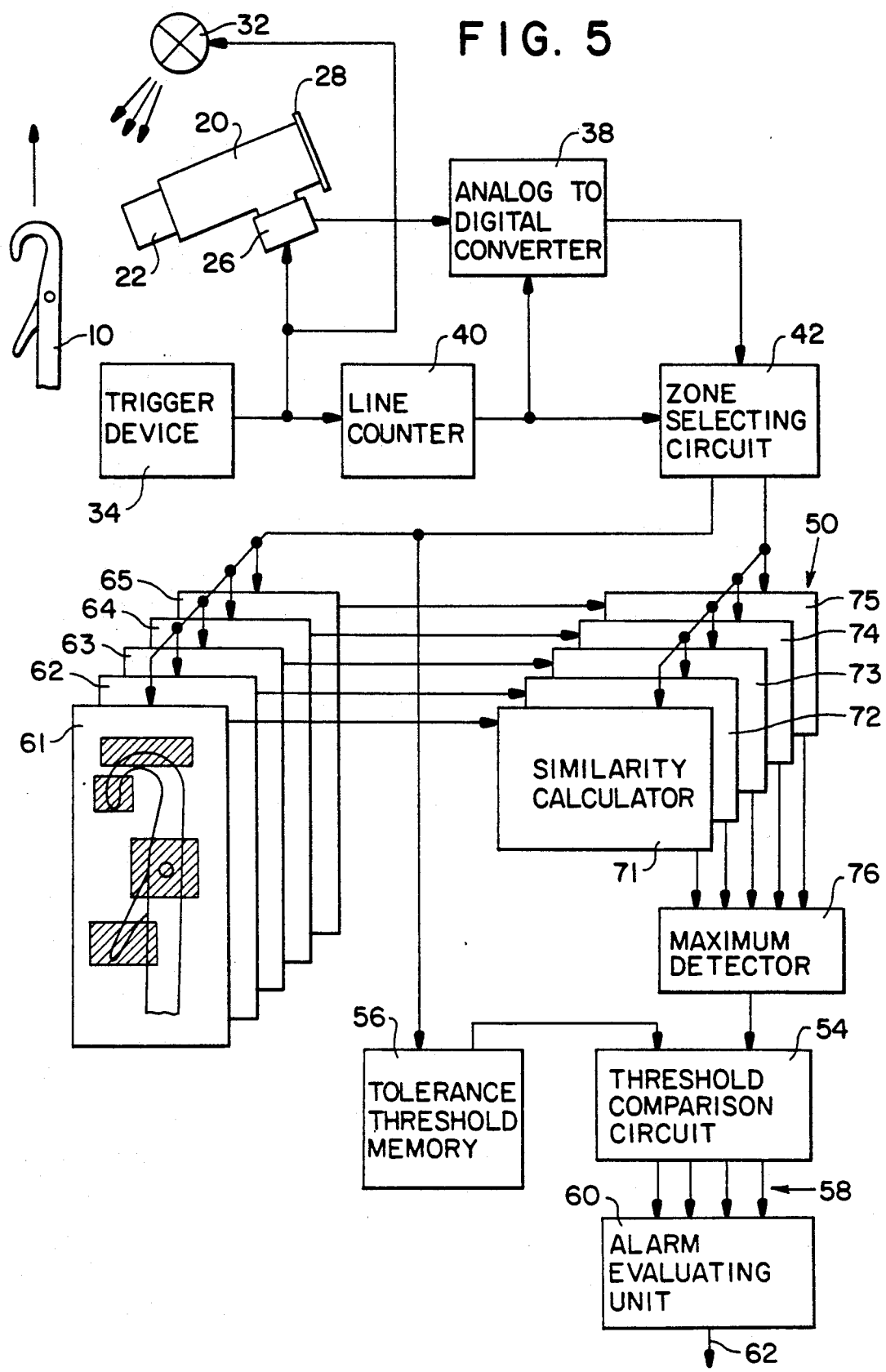
Figure 6:
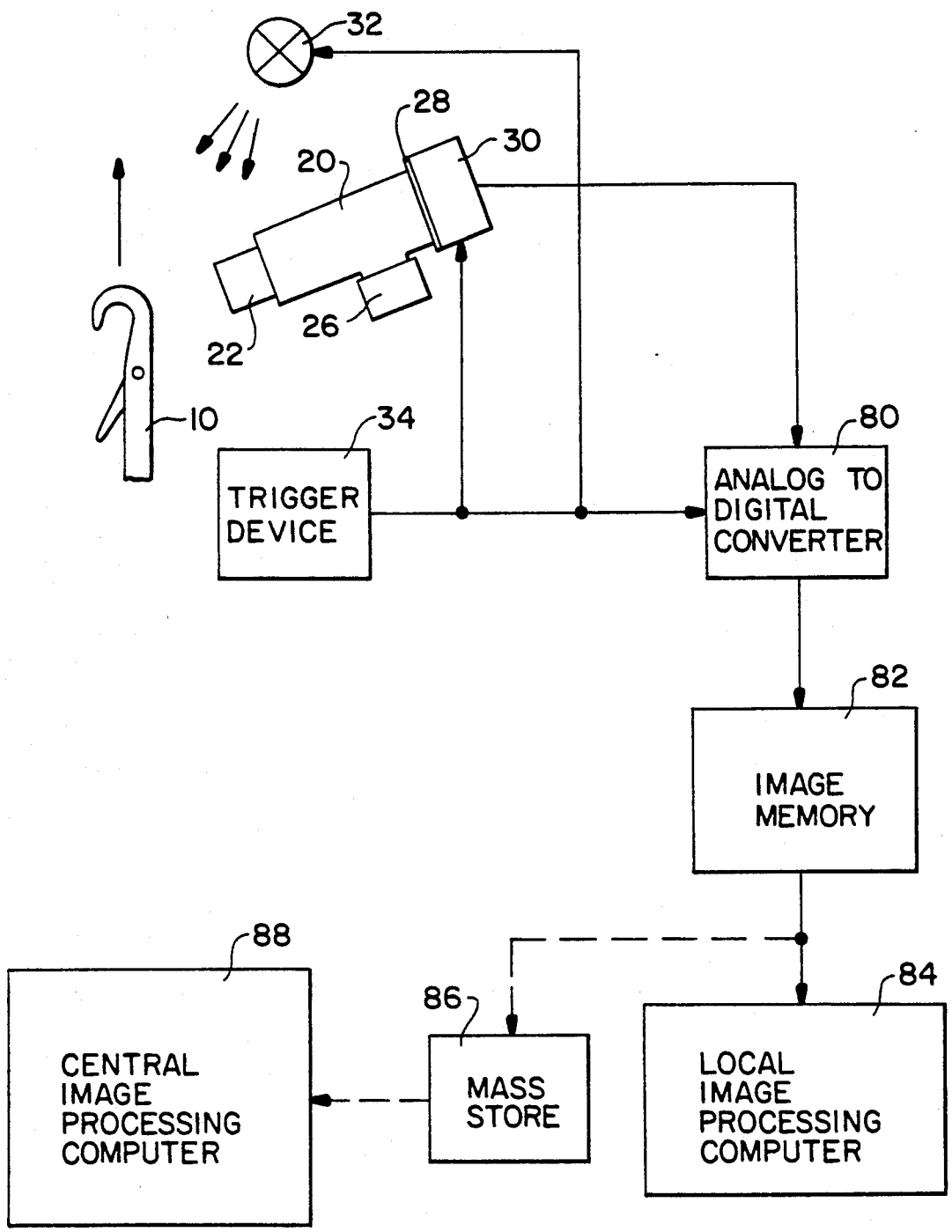

Further features and advantages of the invention will be apparent from the following description of an example of embodiment with the aid of the drawings, wherein:

FIG. 1 is a side elevation of the upper portion of a latch needle of a knitting machine, the zones in which major faults frequently occur being hatched, FIG. 2 shows the latch needle of FIG. 1, the zones in which wear and fine cracks frequently occur being hatched, FIG. 3 shows schematically an image sensor camera for the optical quality control of the needles of a knitting machine, FIG. 4 is a block circuit diagram of an arrangement for monitoring the needles of a knitting machine for the occurrence of major faults with the aid of the image sensor camera or FIG. 3, FIG. 5 is the block circuit diagram of a modified embodiment of the arrangement of FIG. 4 and FIG. 6 is the block circuit diagram of an arrangement for carrying out wear measurements and detecting minor faults in the needles of a knitting machine with the aid of the image sensor camera of FIG. 3.

FIG. 1 shows the upper part of a needle 10 of a knitting machine; illustrated as example is a typical latch needle having a shank 12, a hook head 14 and a latch 18 pivotally mounted on the shank 12 by means of a rivet 16. The zones in which major faults such as breakages, coarse cracks and bends frequently occur are hatched. These zones lie in the upper portion and at the tip of the hook head 14, in the region of the shank 12 perforated to receive the rivet 16 and at the free end of the latch 18. A broken or bent needle causes runs or similar defects; the major fault must therefore be detected immediately at full working speed to enable the knitting machine to be stopped without delay to avoid producing defective goods. Furthermore, the faulty needle must be identified and the nature of the fault classified to enable the fault to be remedied as quickly as possible. In the optical monitoring of needles for the occurrence of such major faults it is possible to utilize the fact that the form of the defective needle is suddenly considerably changed due to the major fault.

FIG. 2 shows the same needle as in FIG. 1 and as example some zones are hatched which are particularly prone to wear and to the occurrence of fine cracks and other minor faults. These zones coincide to some extent with the critical major fault zones illustrated in FIG. 1. Wear faults and fine cracks occur gradually and develop slowly; they are therefore considerably harder to detect than major faults because they change the form of the needles only very slightly and slowly. On the other hand, initially wear faults and fine cracks hardly impair the production quality of the fabrics. It is therefore not necessary to monitor the needles continuously for wear and minor faults during normal operation at full working speed; on the contrary, it suffices to carry out wear measurements and inspections for minor faults, preferably with the machine running slowly, on the needles at relatively large intervals of time during special inspection times.

FIG. 3 shows schematically an image sensor camera 20 which serves both for continuous monitoring of the needles for the occurrence of major faults at full working speed and for periodic detection of wear and fine cracks at relatively large intervals of time. The camera 20 includes an optical system 22 with the aid of which an image of the needle 10 is acquired, and a beam divider 24 which is arranged in the beam path of the optical system 22 and can be formed by a semitransparent mirror or a divider prism. The beam path reflected at the beam divider is directed onto a coarsely resolving image sensor 26 which serves for continuous monitoring of the needles for major faults. The beam path transmitted by the beam divider 24 leads to the exit of the camera 20 provided with a flange 28. In the case of inspection a highly resolving image sensor 30 is attached to the flange 28 and serves to measure wear and detect other minor faults such as fine cracks.

The camera 20 is mounted on the knitting machine in such a manner that the particular needle moved for stitch formation is disposed at the image acquisition point and thus in each cycle the images of all the needles are acquired consecutively. This can be achieved in a circular knitting machine with rotating needle bed in particularly simple manner because in such a machine the stitch formation always takes place at the same point, to which the needles are consecutively brought. The camera can therefore be fixedly arranged and set to the stitch forming point. On the other hand, in flat knitting machines either the camera must be moved relatively to the needle bed or the image of the particular needle moved must be transmitted by means of a system of moving deflection mirrors or the like to a stationarily disposed camera.

When the camera 20 consecutively acquires all the needles on each formation of a course, it operates with the full needle frequency; with a needle frequency of 10 kHz it furnishes 10000 images per second. It is also possible to operate the camera 20 with a divisor of the needle frequency. If for example in the formation of a stitch course only every other needle is acquired and the needles therebetween are acquired during the formation of the next course, the camera 20 operates with half the needle frequency (divisor 2) and furnishes only 5000 images per second. In corresponding manner the divisor 3 could be used by acquiring in the formation of a course only every third needle, and so on. However, the greater the divisor the greater the danger that on sudden occurrence of a major fault several defective courses will be formed before the fault is detected and the machine can be stopped.

Preferably, the optical system 22 is telecentric, i.e. formed with a beam path in which the governing diaphragm is arranged in one of the two focal points. As is known, a telecentric optical system has the property that when the range of the object changes the magnitude of the image remains constant. Thus, the use of a telecentric optical system makes it possible with varying distance between needle and optical system to retain a constant imaging scale.

FIG. 4 shows the block circuit diagram with the components for the real time monitoring of major faults by means of the coarsely resolving image sensor 26. The needle 10 moves in front of the optical system 22 of the camera 20 with a speed of the order of magnitude of 1 m/s in the direction indicated by the arrow. To ensure that in spite of the high needle speed a sharp image of the needle is obtained the exposure is preferably carried out with a stroboscopically pulsed light source 32. For this purpose a semiconductor light source is preferably used generating light in the near infrared range so as both to avoid visible flashes troublesome to humans and shut out any foreign light. As illustrated in FIG. 4 the exposure can be made by reflected light or also by direct light by arranging the light source on the side of the needle 10 opposite the optical system 22. The image of the needle 10 must always be acquired at exactly the same needle position. For this purpose a trigger device 34 is provided which synchronously with the needle movement triggers the stroboscopic light source 32 and the reading out of the image sensor 26 always at the same needle position.

In FIG. 1 the rectangular frame 36 indicates the outline o the image region which on each triggering of the stroboscopic light source 32 is covered by the optical system 22 and the image sensor 26. This image region contains all the hatched regions to be monitored for major faults. With a typical needle motion frequency of 10 kHz the image sensor 26 must be able to convert at least 10000 images per second to electrical image signals. With needle head dimensions in the millimetre range an image-generating acquisition is necessary with a transverse resolution of about 12 to 64 pixels to enable major faults to be detected with adequate certainty. This means that the image region defined by the frame 36 in FIG. 1 must be broken down into 12 to 64 pixels in the transverse direction.

To fulfill these conditions, for the coarsely resolving image sensor 26 preferably one of the columnwise simultaneously readable semiconductor matrix sensors of the type developed for the OCR method ("Optical Character Recognition") with manual reading guns is used. A suitable image sensor of this type is the sensor RA3812P of the company EG&G Reticon which operates with an array of 12 columns which can be read out in parallel and each consist of 38 pixels. The side ratio 12:38 corresponds substantially to the image region defined by the frame 36 in FIG. 1. This image region is scanned by said image sensor in 38 horizontal lines each of 12 pixels, the 12 pixel signals belonging to the same line being read out parallel. Another suitable image sensor of the same series of the company EG&G Reticon is the sensor RA6464N having an array of 64 columns which can be read out in parallel and each consist of 64 pixels. With both image sensors by groupwise reading out of pixels up to 24500 images per second can be obtained.

Connected to the output of the image sensor 26 is an analog to digital converter 38 which converts the analog brightness signals supplied by the image sensor 26 to a series of digital pixel signals. Each digital pixel signal represents the digitally coded brightness value of a pixel of the image area acquired. The output of the trigger device 34 is connected not only to the stroboscopic light source 32 and the image sensor 26 but also to a line counter 40 which is started by the trigger signal furnished by the trigger device 34 simultaneously with the start of the image readout. The output signals of the line counter 40 are supplied on the one hand to the analog to digital converter 38 and on the other to a zone selecting circuit 42 which also receives the digital pixel signals furnished by the analog to digital converter 38.

The zone selecting circuit 42 includes a memory which is programmable by the user and in which the image zones which are to be monitored as test zones are defined. In FIG. 1 as example four rectangular test zones 44, 45, 46, 47 are marked which contain the hatched major fault zones and can be stored in the zone selecting circuit 42. Under the control of the output signals of the line counter 40 the zone selecting circuit 42 blocks all the digital pixel signals not belonging to one of the test zones 44, 45, 46, 47 monitored. The digital pixel signals which are not blocked are transmitted to a processing unit 50.

A reference memory 52 contains for each test zone to be monitored a storage area in which the digital brightness values of a good needle zone are stored pixelwise as reference image as indicated symbolically in FIG. 4. These storage areas are read out under the control of the zone selecting circuit 42 synchronously with the transmitted digital pixel signals of the instantaneously acquired test image and the digital pixel signals thereby emitted at the output of the reference memory 52 are likewise transmitted to the processing unit 50. The pixel signals of all pixel pairs which belong to the same test zone on the one hand in the test image acquired by the camera 20 and on the other in the reference image stored in the reference memory 52 are compared in the processing unit 50 which calculates a similarity degree on the basis of this comparison. Known similarity quantities are the correlation coefficient and the magnitude of the summated differences; the generation and calculation of these similarity degrees is known to the person skilled in the art of image processing. The processing unit 50 furnishes at the output similarity signals which represent degrees of similarity calculated consecutively for the various test zones. Each similarity signal shows the degree of the similarity of the test zone of the test image just acquired and the corresponding test zone of the reference image stored in the reference memory 52. Connected to the output of the processing unit 50 is a threshold comparison circuit 54 which receives the similarity signals.

In a tolerance threshold memory 56 for each test zone an associated tolerance threshold which can be entered by the user is stored. The user can thus set individual tolerance thresholds for the various test zones. The stored tolerance thresholds are consecutively read out under the control of the zone selecting circuit 42 and supplied to the threshold comparison circuit 54 in such a manner that in said threshold comparison circuit 54 on each arrival of a similarity signal associated with a test zone the tolerance threshold associated with the same test zone is also available. The threshold comparison circuit 54 has a plurality of outputs 58 which are allocated to the various test zones. It compares each similarity signal furnished by the processing unit 50 with the tolerance threshold allocated to the same test zone and at the output 58 allocated to the test zone emits a preliminary alarm signal if it is determined by the comparison that the similarity degree between the test image and the reference image of the respective test zone does not reach the tolerance threshold. The outputs 58 of the threshold comparison circuit 54 are connected to an alarm evaluating unit 60 which evaluates all the preliminary alarm signals obtained for an image scanning and in accordance with a weighting of the individual preliminary alarm signals predefinable by the user decides whether a main alarm signal is to be output at an output 62.

Since each output 58 of the threshold comparison circuit 54 is allocated to a specific test zone the output at which a preliminary alarm signal appears also indicates in which test zone a major fault has been detected. This makes it possible to classify the nature of the major fault.

The units illustrated in FIG. 4 operate with the flow pixel signals continuously supplied by the image sensor via the analog to digital converter; storing takes place only in the image sensor 26 where the analog optical image of the needle obtained by the stroboscopic exposure is stored in the form of charges in the semiconductor matrix. A digital image memory is thus superfluous, thus eliminating the computing time and additional cost required by such a memory. At the end of the image readout cycle the decision is available whether or not a main alarm must be given; the system described thus operates in real time at full machine speed. Due to the digital technology employed it is trouble free and flexible and can be economically implemented- The position, size and number of test zones and the individual tolerance thresholds for each zone can be freely fixed by the user; this permits a flexible adaptation of the system to a great number of differently shaped needle types to be inspected at different points.

Due to the telecentric imaging needle oscillations in the direction of the optical axis of the image sensor camera 20 do not result in any scale change and thus do not produce any false alarms. On the other hand, in spite of a satisfactory needle tested lateral oscillations thereof transversely of the optical axis can lead to inadmissible deviations between the test zones of the acquired test image and the reference images of said test zones stored in the reference memory 52 and thereby trigger false alarms. FIG. 5 shows a modified embodiment of the arrangement of FIG. 4 with which the initiation of false alarms by lateral needle oscillations is avoided.

The arrangement of FIG. 5 differs from that of FIG. 4 in that instead of the single reference memory 52 of FIG. 4 several reference memories are provided; as example five reference memories 61, 62, 63, 64, 65 are shown. In these reference memories different reference images are stored for the individual oscillation states. This may for example be done automatically in a training phase in which firstly the ideal reference image of an oscillation-free needle is obtained by acquiring in a first cycle consecutively the images of all the needles of the needle bed and adding up the zone images obtained for averaging. This ideal reference image is stored in the reference memory 61. In further cycles the zone images of the individual needles having different deviations from the ideal reference image are then stored in the further reference memories 62 to 65. In the example of embodiment of FIG. 5 five different reference images of each zone can therefore be stored and can be considered representative reference images of five oscillation states.

The reference memories 61 to 65 are read out in parallel under the control of the zone selecting circuit 42 and the digital pixel signals of the various reference images of each zone thereby obtained are transmitted in parallel to the processing unit 50 and in the latter simultaneously compared with the digital pixel signals of the test image of the respective zone coming from the zone selecting circuit 42, a separate similarity degree being formed for each comparison. This is indicated in FIG. 5 by the processing unit 50 containing five similarity calculators 71, 72, 73, 74, 75. The similarity degrees furnished by the five similarity calculators 71 to 75 are supplied to a maximum detector 76 which selects the similarity degree indicating the best similarity between the test image and the reference image and transfers said degree to the threshold comparison circuit 54 which therefore compares only this similarity degree with the tolerance threshold stored in the tolerance threshold memory 56. This procedure ensures that images which are not similar and occur due to instantaneous oscillations of the needle are excluded from the evaluation of the similarity and therefore do not lead to false alarms. Due to the large number of needles inspected per shift the false alarm probability must be extremely low. If for example at the most one false alarm per eight hour shift is permissible with a machine having a needle frequency of 10000 needles/s the false alarm probability must not be greater than about 1:300,000,000. By increasing the number of reference memories beyond the number 5 given as example in FIG. 5 the effect of chance non-coincidings of test image and reference image can be effectively reduced.

FIG. 6 shows the block circuit diagram with the components for detecting wear faults and fine cracks with the aid of the highly resolving image sensor 30 which for this purpose is mounted on the flange 28 of the camera 20. The highly resolving image sensor 30 has to be used because with the small size of the needle heads, which is in the millimetre range, for effective detection of the wear the image of the needle must be acquired with at least 500 pixels over the entire needle width. The use of vertically arranged line sensors is problematical because the two-dimensional accuracy of a line image made up of individual image lines depends on the speed of the knitting machine, i.e. the rotary speed of a circular knitting machine or the linear speed of a flat knitting machine, being constant and exactly known. However, in reality these speeds are neither constant nor exactly known. For these reasons for the highly resolving acquisition of the wear data a matrix image sensor is used having a resolution of for example $512 \times 512$ to $1300 \times 1100$ pixels. Such image sensors can be read out only with about 25 to 100 images per second. Since wear measurements represent preventative maintenance steps it is admissible for them to be carried out at relatively large intervals of time with the machine running slowly.

Consequently, the wear inspection is not incorporated into the real time system of FIG. 4 or 5 but is designed as offline maintenance system. When a wear test is to be carried out the highly resolving image sensor 30 is secured to the flange 28 of the camera 20 and with the machine running slowly for each needle 10 an image of the visible needle surface is acquired at a predetermined position of the needle governed by the trigger device 34. The analog image signals furnished by the image sensor 30 are digitized in an analog to digital converter 80, each analog pixel signal being converted to a multibit digital code group indicating the grey value of the pixel. The digital pixel signals furnished by the analog to digital converter 80 are stored in an image memory 82. The grey value image stored in this manner in the image memory 82 is then evaluated by known methods of image processing, such as geometrical measuring at interpolated contours, automatic assessment of the surface by texture analysis, etc., in order to detect wear or fine cracks. This analysis can take place in situ in the rhythm of the image acquisition with the aid of a local image processing computer 84. Optionally, the maintenance engineer can also store a collection of grey value images digitally in a mass store 86, such as a magnetic disc, an optical disc or the like, which can later be evaluated in a central imaging processing computer 88, or alternatively the analog output signals of the image sensor camera 20 or the digital pixel signals furnished by the analog to digital converter 80 can be transferred directly to the central image processing computer 88. By this concentration of the complicated high-resolution image processing necessary on numerous knitting machines in a single central image processing computer sophisticated methods of image processing and artificial intelligence can be employed with the greatest possible economy.

As in the real time method for detecting major faults explained with reference to FIG. 4 and 5, the high-resolution wear test can also be restricted to particularly wear-prone needle zones, for example to the test zones 91, 92, 93, 94 and 95 marked in FIG. 2. This makes it possible to reduce the storage requirement in the image memory 82 and possibly in the mass memory 86 and shorten the processing time.

Instead of flanging the highly resolving image sensor 30 at the second beam divider exit of the camera used for the inspection for major faults, it is of course also possible to provide the highly resolving image sensor with its own optical system and to attach it on a mounting means provided for this purpose for the duration of the wear inspection.

I claim:

1. A method for optical quality control of needles of a knitting machine which in the operation of the knitting machine are successively and individually moved from a rest position to a stitch forming position, each needle having at least one critical portion in which faults may occur, said method comprising the steps of acquiring a test image of each needle by means of an image sensor camera when said particular needle is moved away from its rest position, converting the analog image signals furnished by said image sensor camera to digital pixel signals, defining within the test image represented by said digital pixel signals test image zones which contain the images of said critical needle portions, processing the digital pixel signals belonging to said test image zones for recovering information on the state of quality of said particular needle, continuously detecting for major faults, such as breakages, coarse cracks and bends of the needles, and automatically generating a reference image corresponding to a non-oscillating and not defected needle; wherein the test images of the needles are acquired during the normal operation of the knitting machine with a coarse image resolution at an image repetition frequency equal to at least one of the number of needles moved away from their test position per unit of time and an integer divisor of said number, the digital pixel signals of said test image zones are compared at the rhythm at which they are supplied by conversion of said analog image signals with corresponding digital pixel signals of at least one store reference image, a quantitative similarity degree is formed on the basis of said comparison, and an alarm signal is generated when said similarity degree does not reach a predetermined tolerance threshold; and wherein test images of all the needles of the knitting machine are acquired by said image sensor camera, the digital pixel signals of corresponding pixels in all said test images are summed to form an average digital pixel signal for each pixel, and the average digital pixel signals are stored as the digital pixel signals of the reference image.

2. Method according to claim 1, wherein the digital pixel signals of the test images of individual needles exhibiting deviations from the basic reference image are stored as further reference images.

3. Method according to claim 1, wherein the acquisition of the test images with coarse image resolution is carried out during the operation of the knitting machine at the full working speed.

4. Method according to claim 1, wherein for the occasional determination of the wear data and gradually developing minor faults, such as fine cracks, the test images are acquired with high image resolution, the digital pixel signals of the test images or the test zones are stored and the stored pixel signals are evaluated for determining at least one of geometrical dimensions of the needles and surface characteristics of the visible needle surfaces.

5. Method according to claim 4, wherein the acquisition of the test images with high resolution takes place at reduced working speed of the knitting machine.

6. Arrangement for optical quality control of needles of a knitting machine which in the operation of the knitting machine are successively and individually moved from a rest position to a stitch forming position, each needle having at least one critical portion in which faults may occur, said arrangement comprising an image sensor camera having an optical system and at least one image sensor, said image sensor camera being arranged on said knitting machine in such a manner that said optical system images the particular needles moving into the stitch forming position onto each image sensor, said arrangement further comprising a trigger device which triggers the acquisition of a test image of said particular needle when said needle reaches a predetermined position identified for all needles to be monitored, an analog to digital converter connected to the output of each image sensor for converting the analog image signals delivered by each image sensor to digital pixel signals, selecting means connected to the output of said analog to digital converter and triggered by said trigger device to select from said digital pixel signals those belong to predetermined test image zones which contain the images of said critical needle portions, and a signal processing circuit connected to the output of said selecting means to process the selected digital pixel signals to obtain information on the state of quality of said particular needle; wherein the image sensor camera includes a beam divider which is arranged in the beam path of the optical system and which on the one hand for continuous detection of major faults such as breakages, cracks and bends of the needles images the image of the needle portion to be monitored acquired by the optical system on a coarsely resolving image sensor with high image readout frequency and on the other hand directs said image to an exit at which a highly resolving image sensor for occasional determination of the wear data and gradually developing minor faults, such as fine cracks, may be disposed.

7. Arrangement according to claim 6, comprising a stroboscopic light source which is triggered by the trigger device synchronously with the image sensor camera and is so arranged that it illuminates the needles to be acquired by the image sensor camera.

8. Arrangement according to claim 6, wherein the image sensor camera for continuous detection of major faults, such as breakages, cracks and bends of the needles, includes a coarsely resolving image sensor with high image readout frequency.

9. Arrangement according to claim 6, wherein the image sensor camera for occasional determination of the wear data and gradually developing minor faults, such as fine cracks, includes a highly resolving image sensor.

10. Arrangement according to claim 9, wherein the signal processing circuit includes an image memory in which the digital pixel signals originating from the highly resolving image sensor are stored and an image computer is provided which processes the stored pixel signals for determining geometrical dimensions of the needles and/or surface characteristics of the visible needle surfaces.

11. Arrangement according to claim 6, wherein the signal processing circuit includes at least one reference memory in which at least one of a reference image of the needle portion to be monitored and reference images of individual test zones of the needle portion to be monitored are stored, and a processing unit which receives the digital pixel signals of the test image coming from the coarsely resolving image sensor and at least one of the digital pixel signals of the reference image and the corresponding reference images read synchronously therewith from the reference memory and by comparison of the digital pixel signals calculates a similarity degree for the test image and for each test zone, and the processing unit is followed by a threshold comparison circuit which compares the similarity degrees with predetermined tolerance thresholds and for each similarity degree which does not reach the associated tolerance threshold furnishes an alarm signal.

12. Arrangement according to claim 12, comprising a tolerance threshold memory in which the individual tolerance thresholds allocated to the various test zones are stored.

13. Arrangement according to claim 11 comprising an alarm evaluating unit which receives all the alarm signals furnished by the threshold comparison circuit and in accordance with a predetermined weighting of the alarm signals decides on the emission of a main alarm signal.

14. Arrangement according to claim 11, wherein the signal processing circuit comprises a plurality of reference memories in which at least one of the reference images of the needle portion to be monitored and reference images of the test zones for different oscillation states and deflections of the needle are stored, all the reference memories are read out simultaneously with the digital pixel signals furnished by the analog to digital converter, the processing unit compares the digital pixel signals furnished by the reference memories in parallel with the digital pixel signals furnished by the analog to digital converter and on the basis of each comparison computes a similarity degree, and the processing unit is followed by a maximum detector which of the simultaneously computed similarity degrees transfers to the threshold comparison circuit only the similarity degree exhibiting the greatest similarity.

15. Arrangement according to claim 11, wherein between the analog to digital converter and the processing unit a zone selecting circuit is inserted which transfers to the processing unit only the digital pixel signals belonging to predetermined test zones of the test image.

16. Arrangement according to claim 15, wherein the zone selecting circuit initiates the reading out of the or each reference memory synchronously with the transferred pixel signals.

17. Arrangement for optical quality control of needles of a knitting machine which in the operation of the knitting mache are successively and individually moved from a rest position to a stitch forming position, each needle having at least one critical portion in which faults may occur, said arrangement comprising an image sensor camera having an optical system and at least one image sensor, and a coarsely resolving image sensor with high image readout frequency, said image sensor camera being arranged on said knitting machine in such a manner that said optical system images the particular needles moving into the stitch forming position onto each image sensor, said arrangement further comprising a trigger device which triggers the acquisition of a test image of said particular needle when said needle reaches a predetermined position identical for all needles to be monitored, an analog to digital converter connected to the output of each image sensor for converting the analog image signals delivered by each image sensor to digital pixel signals, selecting means connected to the output of said analog to digital converter and triggered by said trigger device to select from said digital pixel signals those belonging to predetermined test image zones which contain the images of said critical needle portions, and a signal processing circuit connected to the output of said selecting means to process the selected digital pixel signals to obtain information on the state of quality of said particular needle, said signal processing circuit comprising a plurality of reference memories in which at least one of reference images of the needle portion to be monitored, reference images of the test zones for different oscillation states and deflections of the needles are stored, and a processing unit which receives the digital pixel signals of the test image coming from the coarsely resolving image sensor and the digital pixel signals of the reference images read synchronously therewith from at least one of the reference memories and by comparison of the digital pixel signals calculates a similarity degree from at least one of the test image and for each test zone, and the processing unit is followed by a threshold comparison circuit which compares the similarity degrees with predetermined tolerance thresholds and for each similarity degree which does not reach the associated tolerance threshold furnishes an alarm signal; wherein reference memories are read out simultaneously with the digital pixel signals furnished by the analog to digital converter, the processing unit compares the digital pixel signals furnished by the reference memories in parallel with the digital pixel signals furnished by the analog to digital converter and on the basis of each comparison computes the similarity degree, and the processing unit is further followed by a maximum detector which o the simultaneously computed similarity degrees transfers to the threshold comparison circuit only the similarity degree exhibiting the greatest similarity.

18. A method for optical quality control of needles of a knitting machine which in the operation of the knitting machine are successively and individually moved from a rest position to a stitch forming position, each needle having at least one critical portion in which faults may occur, said method comprising the steps of acquiring a test image of each needle by means of an image sensor camera when said particular needle is moved away from its rest position, converting the analog image signals furnished by said image sensor camera to digital pixel signals, defining within the test image represented by said digital pixel signals test image zones which contain the images of said critical needle portions, processing the digital pixel signals belonging to said test image zones for recovering information on the state of quality of said particular needle, continuously detecting for major faults, such as breakages, coarse cracks and bends of the needle; wherein the test images of the needles are acquired during the normal operation of the knitting machine with a coarse image resolution at an image repetition frequency equal to at least one of the number of needles moved away from their test position per unit of time and an integer divisor of said number, the digital pixel signals of said test image zones are compared at the rhythm at which they are supplied by conversion of the analog image signals with corresponding digital pixel signals of at least one stored reference image the digital pixel signals of said test image zones are compared simultaneously with the pixel signals of a plurality of stored reference images which correspond to at least one of different oscillation and deflection states of the needles, a quantitative similarity degree is formed on the basis of said comparison, and an alarm signal is generated when said similarity degree does not reach a predetermined tolerance threshold; and wherein only the similarity degree indicating the greatest similarity is subjected to the comparison with the predetermined tolerance threshold.

* * * * *